United States Patent
Muennich

(10) Patent No.: US 9,435,450 B2
(45) Date of Patent: Sep. 6, 2016

(54) PRESSURE DIFFERENTIAL RELIEF VALVE

(71) Applicant: Terumo Cardiovascular Systems, Inc., Ann Arbor, MI (US)

(72) Inventor: Gregory Peter Muennich, Georgetown, MD (US)

(73) Assignee: Terumo Cardiovascular Systems, Inc., Ann Arbor, MI (US)

( * ) Notice: Subject to any disclaimer, the term of this patent is extended or adjusted under 35 U.S.C. 154(b) by 353 days.

(21) Appl. No.: 14/171,925

(22) Filed: Feb. 4, 2014

(65) Prior Publication Data

US 2015/0219230 A1 Aug. 6, 2015

(51) Int. Cl.
*F16K 17/196* (2006.01)
*A61M 39/24* (2006.01)

(52) U.S. Cl.
CPC ............ *F16K 17/196* (2013.01); *A61M 39/24* (2013.01); *A61M 2039/2493* (2013.01); *Y10T 137/0379* (2015.04); *Y10T 137/7773* (2015.04)

(58) Field of Classification Search
CPC .................. B60K 15/03519; B60K 15/03585; B65D 51/1633; B65D 51/1644; B65D 51/16; F16K 17/196; F16K 17/04; F16K 17/0446; F16K 17/046; A61M 39/24; A61M 2039/2493; F01P 11/0238
USPC ............ 220/203.24, 203.02, 203.23, 203.28, 220/203.01, 202, 203.19; 251/281, 324, 251/321, 239, 244, 320, 238, 242; 141/3, 8, 141/20, 65, 95, 325, DIG. 2; 137/493, 493.8
See application file for complete search history.

(56) References Cited

U.S. PATENT DOCUMENTS

| | | | | |
|---|---|---|---|---|
| 1,856,996 | A * | 5/1932 | Heise | F16K 17/196 137/493.8 |
| 2,005,813 | A * | 6/1935 | Thorsen | G05D 16/103 137/494 |
| 2,721,575 | A | 10/1955 | Gier et al. | |
| 3,850,195 | A | 11/1974 | Olsson | |
| 4,171,712 | A * | 10/1979 | DeForrest | F16K 17/196 137/513.5 |
| 7,779,818 | B2 * | 8/2010 | Wilson | F02M 37/20 123/514 |
| 8,632,049 | B2 * | 1/2014 | Stefina | F16K 27/12 215/280 |
| 8,869,826 | B2 * | 10/2014 | Chappel | A61M 27/006 137/504 |
| 2005/0028869 | A1 * | 2/2005 | Roth | F16K 17/196 137/493.4 |
| 2006/0213562 | A1 * | 9/2006 | Jacobson | F15B 13/024 137/493 |
| 2011/0278775 | A1 * | 11/2011 | Germano | F16K 17/18 267/64.23 |
| 2013/0087729 | A1 * | 4/2013 | Bento | F15B 13/0402 251/282 |

* cited by examiner

*Primary Examiner* — Robert J Hicks
(74) *Attorney, Agent, or Firm* — Fish & Richardson P.C.

(57) ABSTRACT

Devices and methods for enhancing the operations of fluid systems are provided. For example, this document provides pressure differential relief valves that are well suited for use with medical fluid reservoirs. The pressure differential relief valves provided herein are described in the context of a medical fluid system, such as an extracorporeal blood flow circuit, but the devices and methods provided herein can be implemented in other types of fluid systems including, but not limited to, pneumatic systems, hydraulic systems, fluid power systems, petroleum systems, and various other types of gaseous or liquid-based fluid systems.

15 Claims, 9 Drawing Sheets

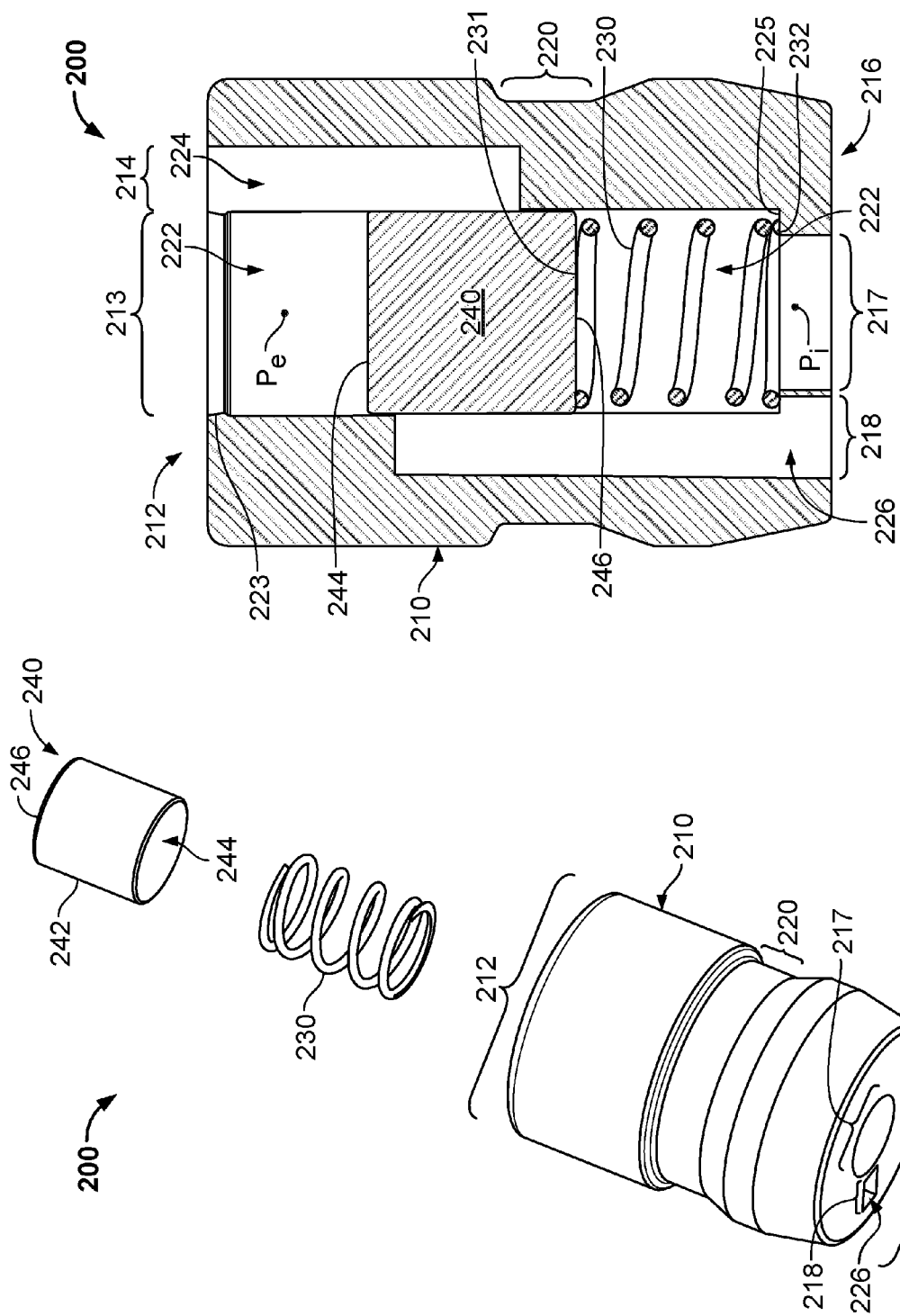

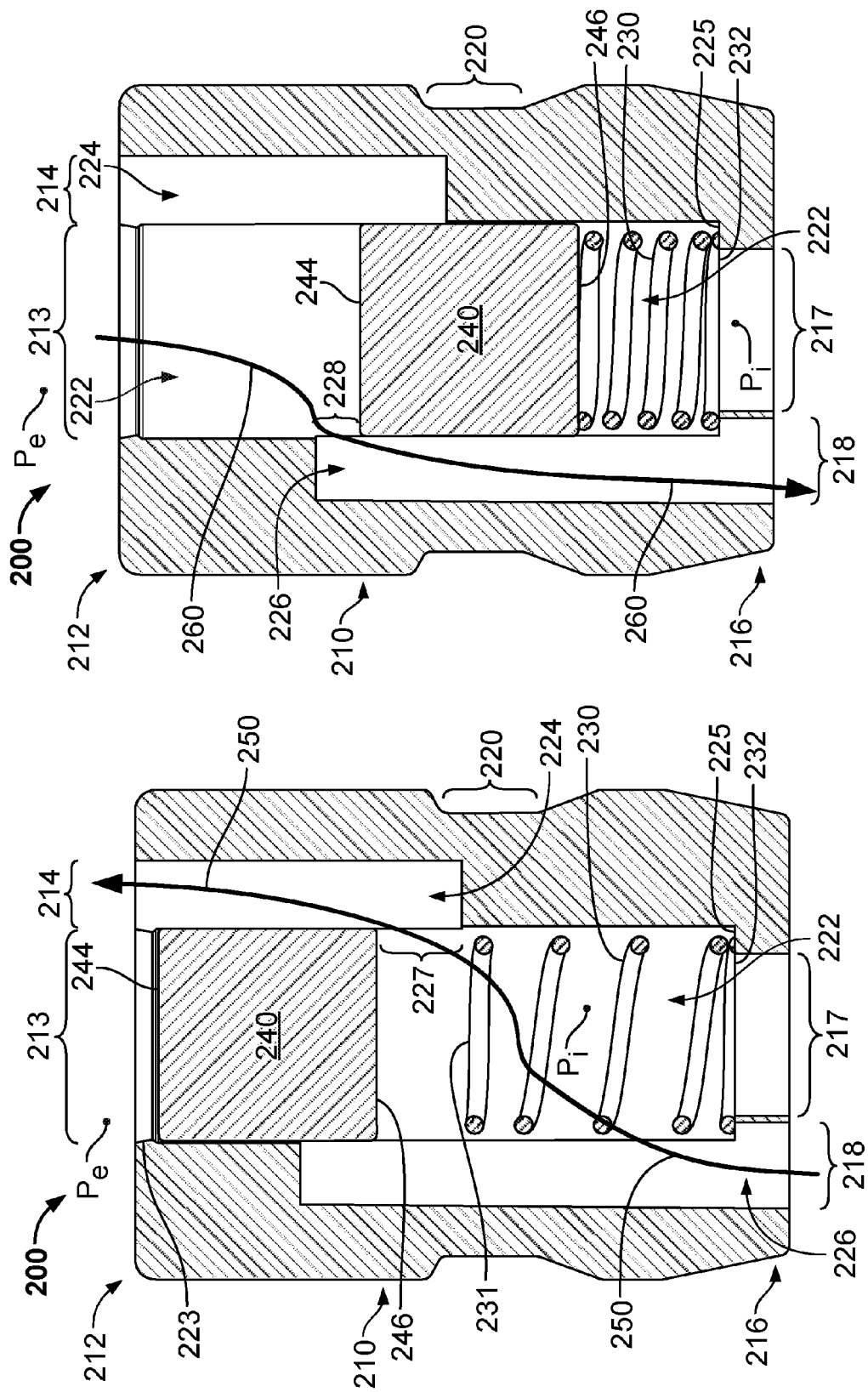

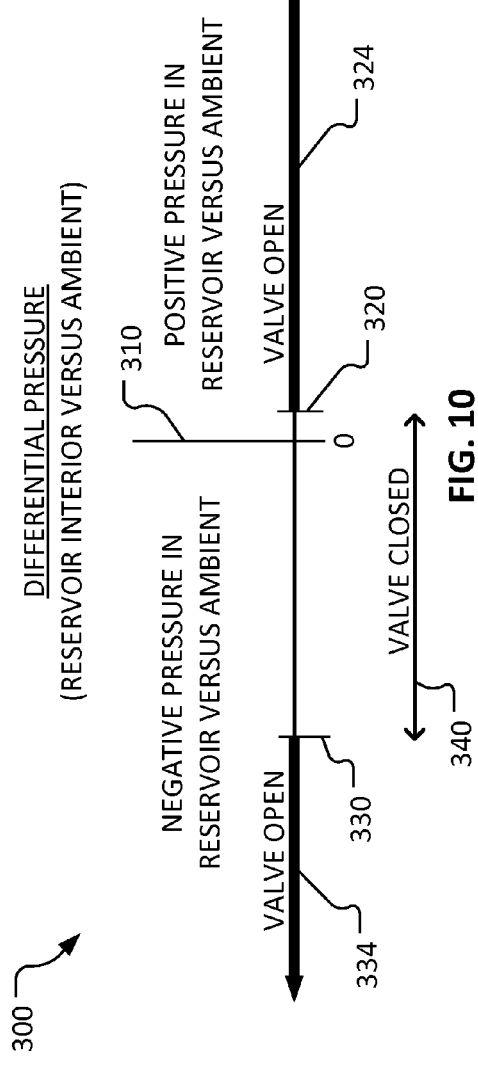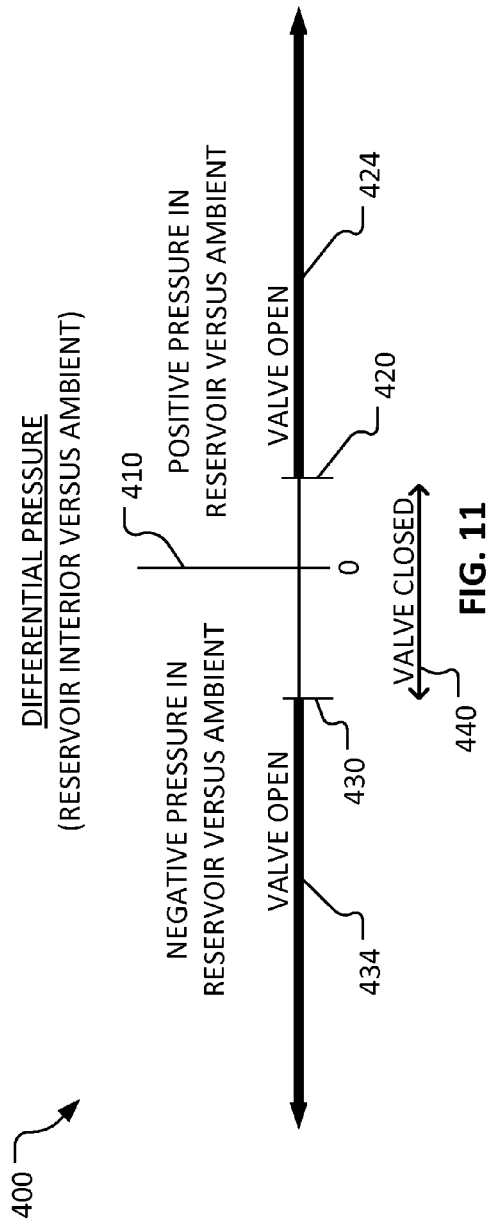

PRESSURE DIFFERENTIAL RELIEF VALVE

BACKGROUND

1. Technical Field

This document relates to devices and methods for enhancing the operations of fluid systems. For example, this document relates to pressure differential relief valves that are well suited for use with medical fluid reservoirs.

2. Background Information

Fluid systems commonly include components such as tubing, pumps, reservoirs, heat exchangers, sensors, filters, valves, and the like. Such components can be connected together in a network to define a fluid flow path. Some fluid systems are open systems, meaning that the fluid flows through the network once and then exits the network. Other fluid systems are closed systems, meaning that the fluid recirculates within the network of components. Fluids are caused to flow in the fluid system using fluid pressure differentials. In some cases, a pump is used to create a pressure differential that causes the fluid to flow within the fluid system. In some cases, a vacuum source is used to create a pressure differential that causes the fluid to flow within the fluid system. In some cases, gravity is used to create a pressure differential that causes the fluid to flow within the fluid system. In some cases, a combination of such techniques is used to create a pressure differential that causes the fluid to flow within the fluid system.

Reservoirs are used as components of fluid systems for various purposes. In some cases, reservoirs are used for accumulation or storage of the fluid. In some cases, the storage of a fluid in a reservoir is used to facilitate a steady outgoing flow of the fluid, despite having an unsteady incoming flow of the fluid. Reservoirs can also be used to facilitate control of the pressure of the fluid within the fluid system. Some reservoirs are completely filled with the fluid, while other reservoirs include an airspace above the level of the fluid in the reservoir.

In some circumstances, the pressure within a reservoir may be higher or lower than the ambient air pressure on the outside of the reservoir. Such pressure differentials can be advantageous when the extent of the pressure differential is within the design parameters of the fluid system. However, in some circumstances the pressure differential between the ambient air and the interior of a reservoir can become greater than intended, and undesirable consequences can result. Such undesirable consequences may include deviating from being in a state of control of the fluid flow, excessive pressure or vacuum levels within the fluid system, damage to the reservoir or another fluid system component, and the like.

Fluid systems are often used in a medical context. Some examples of fluid systems used in the medical context include respiratory systems, anesthesia systems, infusion pump systems, blood transfusion circuits, kidney dialysis systems, extracorporeal membrane oxygenation (ECMO) systems, extracorporeal circuits for heart/lung bypass, and the like. Some such medical fluid systems include the use of medical fluid reservoirs.

As with other types of fluid reservoirs, medical fluid reservoirs may experience a pressure differential between the ambient air and the interior of the medical fluid reservoir that is greater than intended. In some cases, excessive differential pressures can result in undesirable consequences that may damage the medical fluid system. Further, in some such circumstances the undesirable consequences can be risky or inherently detrimental to the health of a patient undergoing treatment using the medical fluid system.

SUMMARY

This document provides devices and methods for enhancing the operations of fluid systems. For example, this document provides pressure differential relief valves that are well suited for use with medical fluid reservoirs.

In general, one aspect of this document features a pressure differential relief valve comprising a valve body having a structure configured to mate with the medical fluid reservoir, a resilient member, and a movable element. The valve body includes a first end portion and a second end portion. The valve body defines an open interior bore space within the valve body. The valve body also defines first and second gas passageways that are configured to allow a first exterior region that is outside of the valve body and proximate to the first end portion to be in fluid communication through the valve body with a second exterior region that is outside of the valve body and proximate to the second end portion. The resilient member is at least partially disposed within the open interior bore space. The movable element is at least partially disposed within the open interior bore space. The movable element is movable within the open interior bore space at least between (i) a first end position that is closer to the first end portion than to the second end portion, (ii) a second end position that is closer to the second end portion than to the first end portion, and (iii) an intermediate position that is between the first and second end positions. When the movable element is in the intermediate position, the movable element substantially prevents fluid communication through the valve body between the first exterior region and the second exterior region. When the movable element is in the first end position, the first exterior region and the second exterior region are in fluid flow communication through at least the first gas passageway. When the movable element is in the second end position, the first exterior region and the second exterior region are in fluid flow communication through at least the second gas passageway, and the movable element has deflected the resilient member.

In various implementations of the pressure differential relief valve, when the atmospheric pressures at the first and second exterior regions are equal the movable element may be biased to be in contact with the resilient member. Optionally, the movable element may be spaced apart from the resilient member when the movable element is in the first end position. In some embodiments, the first end portion defines a first end opening and the second end portion defines a second end opening. An atmospheric pressure at the first exterior region can be exerted on a first surface of the movable element at least through the first end opening to thereby urge the movable element to move towards the second end position, and an atmospheric pressure at the second exterior region can be exerted on a second surface of the movable element at least through the second end opening to thereby urge the movable element to move towards the first end position.

In various implementations of the pressure differential relief valve, the valve may be configured such that differences between the atmospheric pressure at the first exterior region and the atmospheric pressure at the second exterior region can cause the movable element to move from the intermediate position to the first or second end position to thereby reduce the differences between the atmospheric pressure at the first exterior region and the atmospheric pressure at the second exterior region. Optionally, the valve body may have an overall longitudinal length that extends directionally between the first and second end portions. The first gas passage way may have a first longitudinal length that extends directionally between the first and second end portions. The second gas passageway may have a second longitudinal length that extends directionally between the first and second end portions. In some embodiments, the first longitudinal length is less than the overall longitudinal length. The second longitudinal length may be less than the overall longitudinal length. In some embodiments, a sum of the first longitudinal length added to the second longitudinal length may be greater than the overall longitudinal length. The movable element may have a length extending directionally between the first and second end portions, and the sum of the first longitudinal length added to the second longitudinal length minus the overall length of the valve body may be less than the length of the movable element. In some embodiments, the resilient member may be a spring. In particular embodiments, the resilient member may be a coil spring.

In a second general aspect, this document features a medical fluid reservoir system. The medical fluid reservoir system comprises a reservoir shell and a differential pressure relief valve that is coupled to the reservoir shell. The reservoir shell defines an interior space inside of the reservoir shell that is configured to contain a medical fluid and an exterior space that is outside of the reservoir shell. The pressure relief valve comprises a valve body, a resilient member, and a movable element. The valve body includes a first end portion at least partially exposed to the exterior space and a second end portion at least partially exposed to the interior space. The valve body defines an open interior bore space within the valve body. The resilient member is at least partially disposed within the open interior bore space. The movable element is at least partially disposed within the open interior bore space. The movable element is movable within the open interior bore space at least between (i) a first end position that is closer to the first end portion than to the second end portion, (ii) a second end position that is closer to the second end portion than to the first end portion, and (iii) an intermediate position that is between the first and second end positions. When the movable element is in the intermediate position, the movable element prevents fluid communication through the valve body between the interior and exterior spaces. When the movable element is in the first end position, the interior and exterior spaces are in fluid flow communication. When the movable element is in the second end position, the interior and exterior spaces are in fluid flow communication, and the movable element has deflected the resilient member.

In some implementations of the medical fluid reservoir system, the valve body may define first and second gas passageways that are each configured to allow the exterior space to be in fluid communication through the valve body with the interior space. Optionally, when the movable element is in the first end position, the interior and exterior spaces may be in fluid flow communication through at least the first gas passageway. Also optionally, when the movable element is in the second end position the interior and exterior spaces may be in fluid flow communication through at least the second gas passageway. In some embodiments, the valve body have an overall longitudinal length extending directionally between the first and second end portions, the first and second gas passageways have longitudinal lengths extending directionally between the first and second end portions, and the lengths of each of the first and second gas passageways may be less than the overall longitudinal length of the valve body. Also, the combined lengths of the first and second gas passageways may be greater than the overall longitudinal length of the valve body. In particular embodiments, the movable element may have a length extending directionally between the first and second end portions, and the combined lengths of the first and second gas passageways minus the overall length of the valve body may be less than the length of the movable element. In some implementations, the medical fluid may comprise blood. Further, the medical fluid reservoir may be optionally configured to have an air space disposed within the interior space in addition to having the blood within the interior space. In some embodiments, the differential pressure relief valve may be configured such that differences between the atmospheric pressure of the exterior space and the atmospheric pressure of the interior space can cause the movable element to move from the intermediate position to the first or second end position to thereby reduce the differences between the atmospheric pressure at the exterior space and the atmospheric pressure at the interior space.

In a third general aspect, this document features a method of relieving a pressure differential between an interior space of a medical fluid reservoir and an ambient space. The method comprises providing a differential pressure relief valve, coupling the differential pressure relief valve to the medical fluid reservoir such that the first end portion is at least partially exposed to the ambient space and the second end portion is at least partially exposed to the interior space, and operating the medical fluid reservoir such that pressure differentials between the interior space and the ambient space can be at least partially relieved by movement of the movable element. The pressure relief valve can be configured as any of the embodiments described elsewhere herein.

In various implementations of the method of relieving a pressure differential between an interior space of a medical fluid reservoir and an ambient space, in response to the medical fluid reservoir having a higher pressure in the interior space than a pressure at the ambient space, the movable element may move to the first end position. In some embodiments, in response to the medical fluid reservoir having a lower pressure in the interior space than a pressure at the ambient space, the movable element may move to the second end position.

Particular embodiments of the subject matter described in this document can be implemented to realize one or more of the following advantages. First, in some embodiments the pressure differential relief valves provided herein may prevent damage to a fluid system by relieving an excessive pressure differential between an interior of a fluid reservoir and an ambient space. Second, the pressure differential relief valves provided herein may facilitate equalization of both positive and negative pressure differentials using a single valve construct. Third, when used in a medical context, some embodiments of the pressure differential relief valves provided herein may prevent harm to a patient that is undergoing treatment using a medical fluid system. Fourth, in some embodiments the pressure differential relief valves provided herein can be manufactured at a low cost, and may therefore be well suited for one-time-use medical fluid reservoirs as is common in the medical context. Fifth, the level of differential pressure at which the pressure differential relief valves provided herein activate to relieve pressure differentials can be readily selected as desired. Sixth, in some embodiments the negative and positive differential pressures at which the differential relief valves activate can be independently established by the selection of valve components having design characteristics as desired.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 4 is an exploded perspective view of an example pressure differential relief valve in accordance with some embodiments provided herein.

FIG. 5 is a longitudinal cross-sectional view of the example pressure differential relief valve of FIG. 4 in an inactivated configuration.

FIG. 8 is a longitudinal cross-sectional view of the pressure differential relief valve of FIG. 4 in a first activated configuration for relieving an excess differential pressure.

FIG. 9 is a longitudinal cross-sectional view of the pressure differential relief valve of FIG. 4 in a second activated configuration for relieving an excess differential pressure.

FIG. 10 is a graph depicting the operations of a pressure differential relief valve that has been configured to activate at particular levels of negative and positive differential pressures.

FIG. 11 is a graph depicting the operations of another pressure differential relief valve that has been configured to activate at particular levels of negative and positive differential pressures that are different than those of the valve depicted in FIG. 10.

Like reference numbers represent corresponding parts throughout.

DETAILED DESCRIPTION

This document provides devices and methods for enhancing the operations of fluid systems. For example, this document provides pressure differential relief valves that are well suited for use with medical fluid reservoirs. While the pressure differential relief valves provided herein are described in the context of a medical fluid system, such as an extracorporeal blood flow circuit, it should be understood that the devices and methods provided herein are not limited to such contexts. Indeed, the pressure differential relief valves and methods provided herein can be implemented in other types of fluid systems including, but not limited to, pneumatic systems, hydraulic systems, fluid power systems, petroleum systems, and various other types of gaseous or liquid-based fluid systems.

Figure 1:
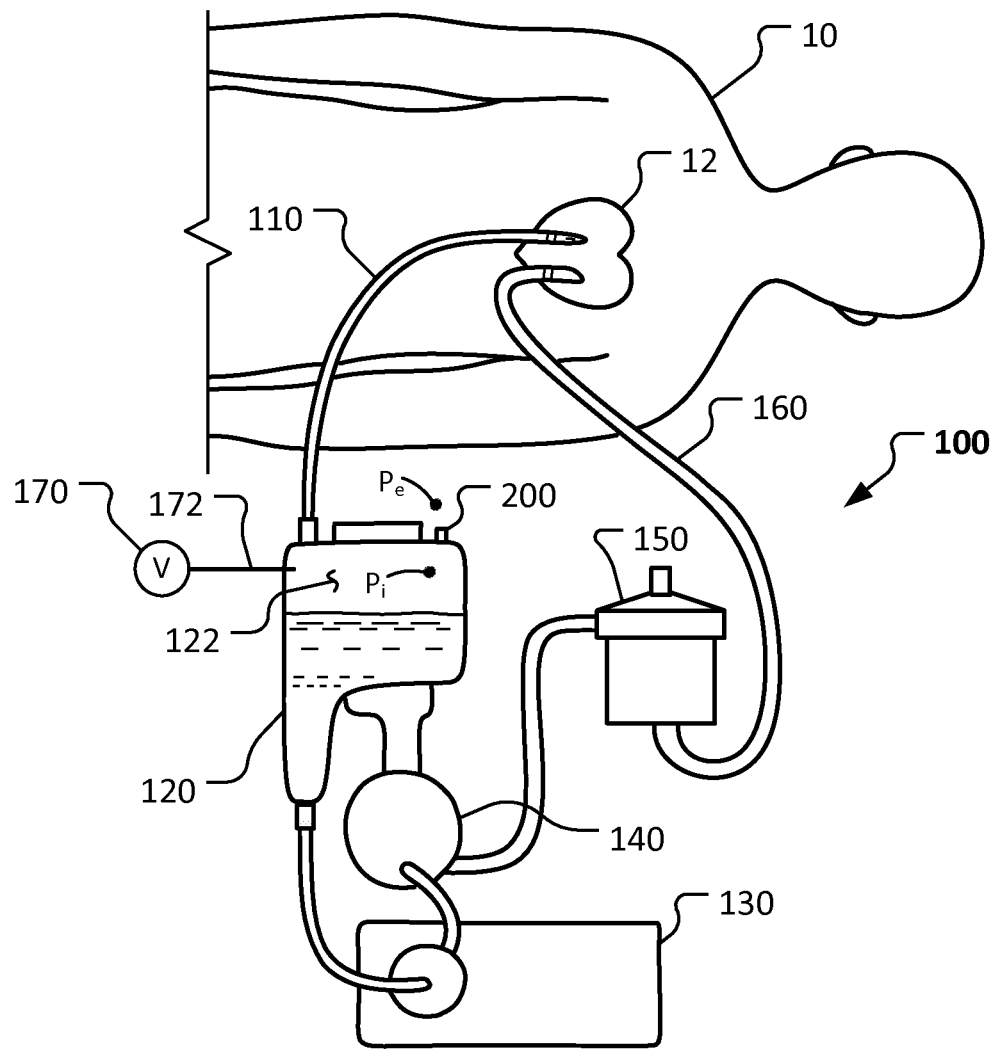
FIG. 1 is a schematic diagram of patient undergoing an example medical procedure using an extracorporeal blood flow circuit that includes a medical fluid reservoir.

Referring to FIG. 1, a patient 10 can receive a medical treatment while using a medical fluid system 100. In this illustrative example, the patient 10 is undergoing a heart bypass procedure using an extracorporeal blood flow circuit 100. The circuit 100 is connected to the patient 10 at the patient's heart 12. Blood from the patient 10 is extracted from the patient 10 at the patient's heart 12; the blood is circulated through the circuit 100; and the blood is then returned to the patient's heart 12.

The extracorporeal blood flow circuit 100 includes, at least, a venous tube 110, a blood reservoir 120, a pump 130, an oxygenator 140, an arterial filter 150, and an arterial tube 160. The venous tube 110 is in physical contact with the heart 12 and in fluid communication with the venous side of the circulatory system of the patient 10. The venous tube 110 is also in fluid communication with an inlet to the reservoir 120. An outlet from the reservoir 120 is connected by tubing to an inlet of the pump 130. The outlet of the pump 130 is connected to tubing to an inlet of the oxygenator 140. The outlet of the oxygenator 140 is connected by tubing to an inlet of the arterial filter 150. An outlet of the arterial filter 150 is connected to the arterial tube 160. The arterial tube 160 is in physical contact with the heart 12 and in fluid communication with the arterial side of the circulatory system of the patient 10.

Briefly, the extracorporeal blood flow circuit 100 operates by removing venous blood from the patient 10 via the venous tube 110. Blood from the venous tube 110 is deposited in the reservoir 120. At least some amount of blood is intended to be maintained in the reservoir 120 at all times during the medical procedure. Blood from the reservoir 120 is drawn from the reservoir 120 by the pump 130. The pressure generated by the pump 130 propels the blood through the oxygenator 140. In the oxygenator 140 the venous blood is enriched with oxygen. The oxygen-rich arterial blood exits the oxygenator 140, travels through the arterial filter 150, and is injected into the patient's heart 12 by the arterial tube 160.

The flow of blood through the extracorporeal blood flow circuit 100 is essentially continuous while the medical procedure is taking place. Within that overall context, an accumulation of blood exists in the reservoir 120 during the procedure. The accumulation of blood within the reservoir 120 serves multiple purposes. In one aspect, the accumulation of blood in the reservoir 120 provides a buffer amount to help ensure a continuous flow of oxygenated blood to the patient 10, even in the event that blood flow to the reservoir 120 is interrupted. In another aspect, the reservoir 120 allows the venous blood to deaerate. The deaeration of the venous blood takes place by allowing air bubbles in the blood to escape the blood and flow into the air. For at least that reason, an airspace 122 is maintained in the reservoir 120.

As described above, the venous blood flows (drains) from the heart 12 to the reservoir 120. In some implementations, the venous blood drainage from the heart 12 to the reservoir 120 occurs primarily as a result of gravity. In such gravity drainage implementations the reservoir 120 is positioned at a lower elevation than the heart 12. In result, the blood naturally flows 'downhill' from the heart 12 to the reservoir 120. In some implementations, a vacuum is drawn in the airspace 122 of the reservoir 120 to assist with the drainage from the heart 12 to the reservoir 120. This technique is known as vacuum assisted venous drainage (VAVD).

During VAVD procedures, the venous drainage is assisted by placing the reservoir 120 under a negative pressure (vacuum) in relation to the ambient pressure. For example, in some implementations a negative pressure is achieved within the airspace 122 using a vacuum source 170 that is connected to the reservoir 120 via a vacuum line 172. The vacuum source 170 is used to reduce an air pressure $P_i$ that is in the interior airspace 122 of the reservoir 120 to less than an air pressure $P_e$ at an ambient location that is externally adjacent to the reservoir 120. To maintain an effective level of vacuum in the airspace 122 when using VAVD, the reservoir 120 is sealed in an essentially airtight manner. Consequently, an air pressure differential may exist between $P_i$ and $P_e$. Under normal operating conditions, the pressure differential between $P_i$ and $P_e$ (e.g., where $P_i<P_e$) is beneficial for assisting with the drainage of blood from the heart 12 to the reservoir 120.

In some scenarios, however, the pressure differential between $P_i$ and $P_e$ can become abnormal, and potentially detrimental consequences can result. For example, in the event that the vacuum line 172 becomes blocked or kinked, vacuum withdrawal of air from the reservoir 120 can stop, and the reservoir 120 (being sealed airtight) can build up a positive pressure at $P_i$ in relation to $P_e$. In that case, it is possible that pressurized air from the airspace 122 can be forced from the reservoir 120, through the venous tube 110, and into the heart 12 of the patient 10. In another example, an excess of vacuum in the reservoir 120 (too high of a pressure differential between $P_i$ and $P_e$) can result if there is a failure of the regulator of the vacuum source 170, or if an incorrect set point is used for the vacuum source 170. In such a case, the excess vacuum in the airspace 122 of the reservoir 120 can pull air across the membrane of the oxygenator 140, causing air to be potentially sent to the patient 10 via the arterial tube 160. In some cases, excess negative pressure can also damage the blood cells. For these and other such reasons, the pressure differential between $P_i$ and $P_e$ can be beneficial when controlled within a desirable range of pressure, but can be detrimental when outside (above or below) the desirable range of pressure. Hence, a pressure differential relief device, that remedies both an excessive vacuum situation and an overpressure situation, can be advantageously used in conjunction with the reservoir 120. The benefits of such a pressure differential relief device can also be realized in the context of fluid circuits other than the example extracorporeal blood flow circuit 100, including in other medical applications and in other applications beyond the medical context.

Figure 3:
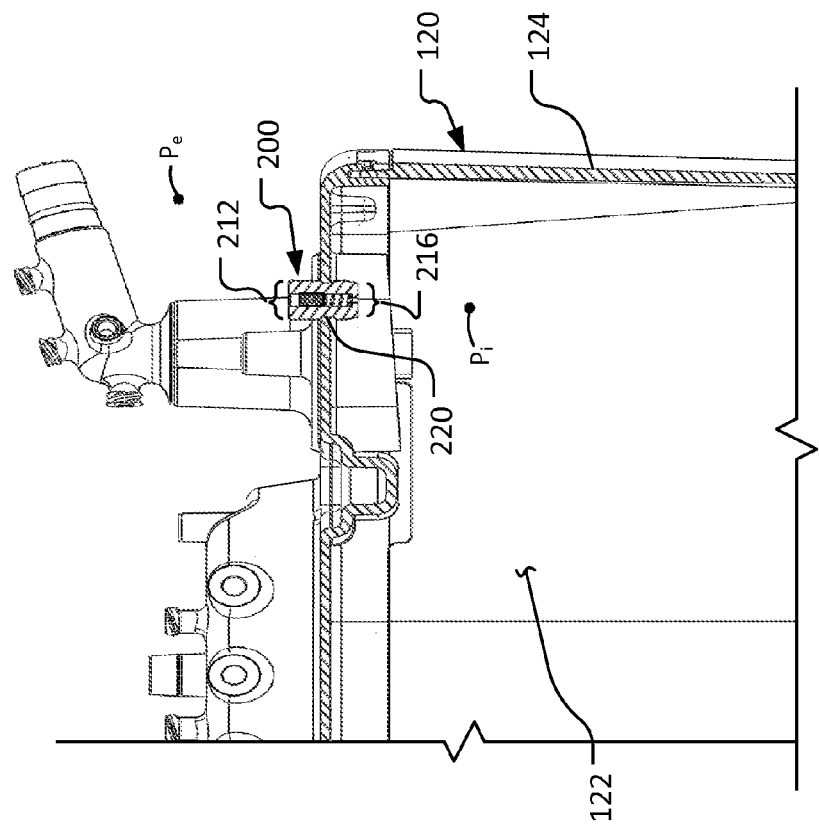
FIG. 3 is partial cross-sectional view of the example medical fluid reservoir and pressure differential relief valve of FIG. 2.
Figure 2:
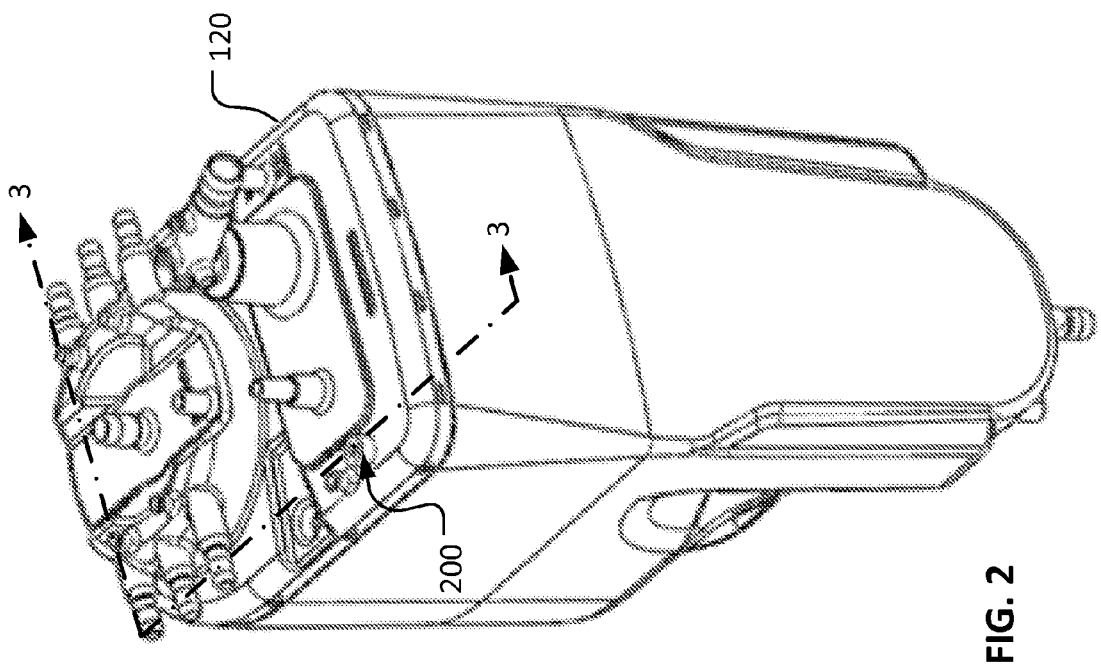
FIG. 2 is a perspective view of an example medical fluid reservoir that includes a pressure differential relief valve in accordance with some embodiments provided herein.
Figure 7:
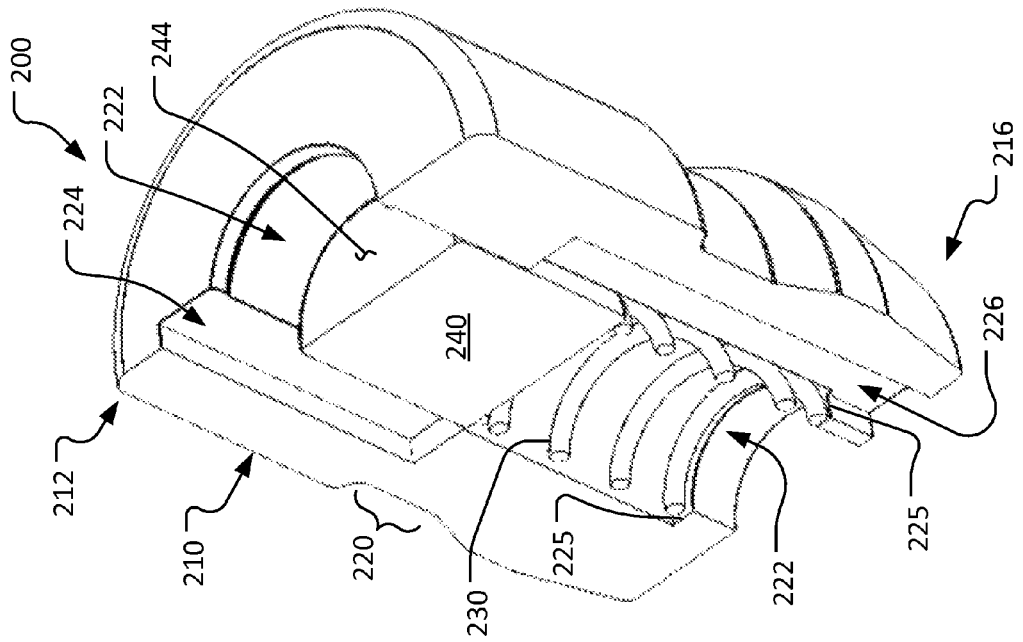
FIG. 7 is a perspective longitudinal cross-sectional view of the example pressure differential relief valve of FIG. 4 in an inactivated configuration.
Figure 6:
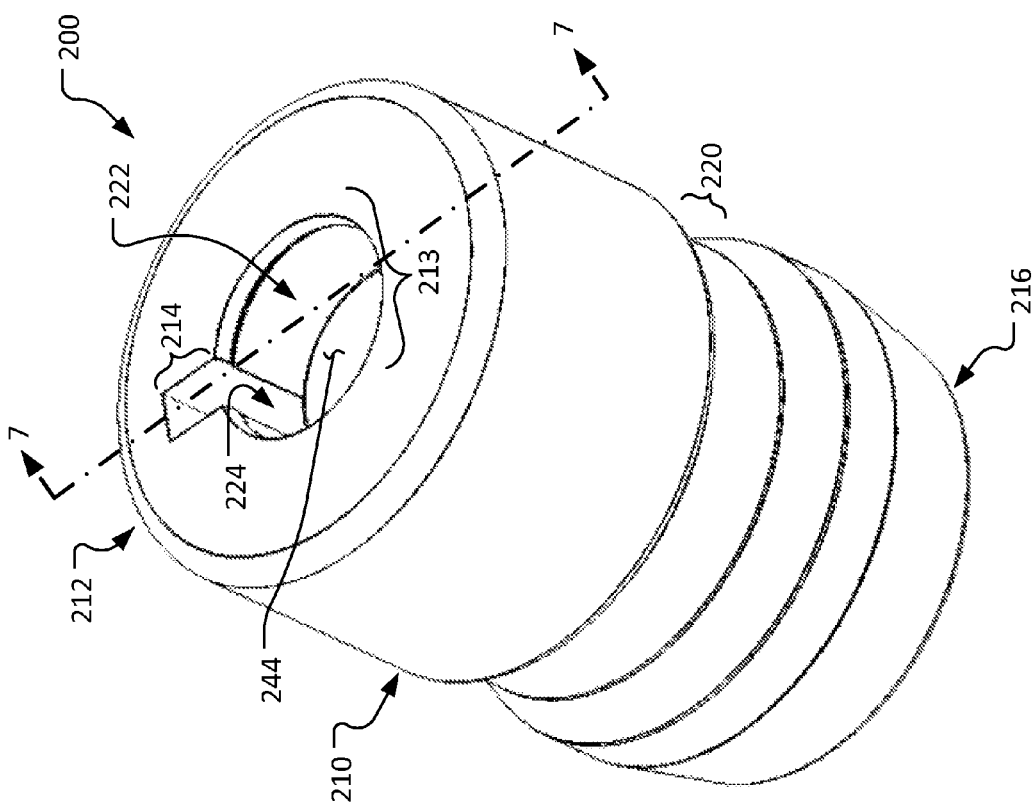
FIG. 6 is a perspective view of the example pressure differential relief valve of FIG. 4.

Referring now to FIGS. 1, 2, and 3, the reservoir 120 can include a pressure differential relief valve 200 (also referred to hereinafter as "valve 200"). As will be described further below, the valve 200 is configured to facilitate equalization of both positive and negative pressure differentials between $P_i$ and $P_e$.

In the depicted embodiment, the valve 200 is engaged with the reservoir's shell 124 (wall). That is, as best seen in FIG. 3, the valve 200 is engaged with the shell 124 such that a middle portion 220 of the valve 200 is in contact with the shell 124. A first end portion 212 of the valve 200 is exposed exteriorly to the reservoir in the ambient space above the interface between the middle portion 220 and the shell 124. A second end portion 216 of the valve 200 is exposed within the interior airspace 122 defined by the reservoir 120.

The valve 200 may be coupled with the shell 124 in a variety of ways including, but not limited to, using a snap fit, an adhesive bond, a weld, a threaded connection, a compression fit, a bayonet connection, a luer fitting, and the like. In some cases, a seal or a gasket, such as one or more O-rings, may be included. In some embodiments, the valve 200 or portions of the valve 200 may be integrally molded with portions of the reservoir 200. In alternative embodiments, the valve 200 may be engaged with the reservoir 120 using a tube, a fitting, a coupling, and the like.

Referring now to FIGS. 4 through 7, the pressure differential relief valve 200 includes a valve body 210, a resilient member 230, and a movable element 240. The resilient member 230 and the movable element 240 are contained within an open interior bore space 222 (also referred to herein as "bore 222") of the valve body 210.

In this embodiment, the resilient member 230 is a coil compression spring, and the movable element 240 is a cylindrical piston. In other embodiments, the resilient member 230 and the movable element 240 may be different types or configurations of components. For example, in some embodiments the resilient member 230 can be open-cell foam, one or more wave washers, and the like. In some embodiments, the movable element 240 can be spherical, rectangular, cubical, ovular, and the like. In some embodiments, a resilient element 230 may be located on each side of the movable element 240.

The valve body 210 includes the first end portion 212, the second end portion 216, the middle portion 220. The first end portion 212 and the second end portion 216 are configured similarly in that they both include an end opening 213 and 217 and a gas passageway external port 214 and 218. The end openings 213 and 217 are both confluent with the bore 222. When the valve 200 is engaged with the reservoir 120 (e.g., as shown in FIG. 3), the first end opening 213 is also confluent with the exterior or ambient space that has the pressure $P_e$, and the second end opening 217 is also confluent with the reservoir's interior airspace 122 that has the pressure $P_i$.

The first gas passageway external port 214 is confluent with the ambient space and with a first gas passageway 224. The second gas passageway external port 218 is confluent with the reservoir's interior airspace 122 and a second gas passageway 226. In some embodiments, the first and second gas passageways 224 and 226 are elongate open channel-like spaces that are defined by the valve body 210 in the interior of the valve body 210. In some such embodiments, the first and second gas passageways 224 and 226 are at least partially confluent with the bore 222.

The depicted embodiment is configured with a single gas passageway external port 214 and a single corresponding gas passageway 224 that are in confluence with the ambient space. Likewise, the depicted embodiment is configured with a single gas passageway external port 218 and a single corresponding gas passageway 226 that are in confluence with the reservoir's interior airspace 122. That said, such a configuration is not required for all valve embodiments, and other configurations are envisioned within the scope of this disclosure. For example, some valve embodiments have two or more discreet external ports, each with a corresponding passageway, that are configured to be in confluence with the internal space of the reservoir. Such a configuration can be advantageous in some circumstances, such as when the external port(s) and passageway(s) may have the potential to become plugged by, for example, the contents of the reservoir. In such circumstances, having two or more external ports and passageways can provide redundancy such that the pressure differential relief valve can continue to function properly even if one external port and passageway becomes plugged. Some valve embodiments have two or more discreet external ports, each with a corresponding passageway, that are configured to be in confluence with the ambient space that is exterior of the reservoir. Some valve embodiments have two of more discreet external ports, each with a corresponding passageway, that are configured to be in confluence with the internal space of the reservoir, as well as two or more discreet external ports, each with a corresponding passageway, that are configured to be in confluence with the ambient space that is exterior of the reservoir. Still referring to FIGS. 4 through 7, the first and second gas passageways 224 and 226 have longitudinal lengths extending directionally between the first and second end portions 212 and 216. The individual lengths of the first and second gas passageways 224 and 226 are less than the overall longitudinal length of the valve body 210. In some embodiments, a sum of the longitudinal length of the first gas passageway 224 added to the longitudinal length of the second gas passageway 226 is greater than the overall longitudinal length of the valve body 210. In other embodiments, the sum of the longitudinal length of the first gas passageway 224 added to the longitudinal length of the second gas passageway 226 is less than the overall longitudinal length of the valve body 210.

The valve body 210 can be made of a polymeric or metallic material. In some embodiments, the valve body 210 is an injection molded thermoplastic. For example, the valve body 210 can be made of materials such as, but not limited to, polycarbonate, polyether ether ketone (PEEK), polyetheramide, polyesters, polysulfone, and the like. The valve body 210 can also be made of metals such as aluminum, stainless steel, steel alloys, and the like. In some embodiments, the valve body 210 can be constructed of a combination of such materials.

The valve body 210 is scalable to a variety of overall lengths and diameters. For example, in some embodiments the overall longitudinal length of the valve body 210 can be anywhere from about 8.0 millimeters to about 38.0 millimeters, or more. In some embodiments, the diameter of the valve body 210 can be anywhere from about 7.0 millimeters to about 35.0 millimeters, or more.

The resilient member 230 is located within the bore 222 and is positioned between the movable element 240 and the second end portion 216. The resilient member 230 has a first end 231 that is in contact with the movable element 240. The resilient member 230 has a second end 232 that is in contact with a second lip 225 of the valve body 210. In some embodiments, the resilient member 230 is not coupled to the movable element 240. In other words, in some embodiments the resilient member 230 and the movable element 240 can be in contact with each other, but are separable from each other.

In the depicted embodiment, the resilient member 230 is a closed end coil compression spring that is made of stainless steel. In some embodiments, the resilient member 230 is made from other materials such as, but not limited to, spring steel, phosphor bronze, beryllium copper, chrome silicon, music wire, titanium, and the like. The outer diameter of the resilient member 230 is sized to be less than the diameter of the bore 222 so that the resilient member 230 is free to move within the bore 222. The spring rate (spring constant) of the resilient member 230 can be, for example, about 0.01 N/mm, about 0.02 N/mm, about 0.03 N/mm, about 0.04 N/mm, about 0.05 N/mm, about 0.06 N/mm, about 0.07 N/mm, about 0.08 N/mm, about 0.09 N/mm, about 0.10 N/mm, or more than about 0.10 N/mm. The spring rate selected can depend on factors such as the size of the valve 200 and the specifications for the level of differential pressure at which the valve is to be activated (opened to relieve the differential pressure).

The movable element 240 can be made of a polymeric, ceramic, or metallic material. In some embodiments, the movable element 240 is an injection molded thermoplastic. In alternate embodiments, the movable element 240 is an extruded material. The movable element 240 can be made of materials such as, but not limited to, polycarbonate, PEEK, polyetheramide, polyesters, polysulfone, and the like. The movable element 240 can also be made of metals such as aluminum, stainless steel, steel alloys, and the like. In some embodiments, the movable element 240 can be constructed of a combination of such materials.

The diameter of the movable element 240 is slightly less than the diameter of the bore 222. Accordingly, the movable element 240 is free to move within the bore 222, while maintaining a substantially airtight seal therebetween. For example, in some embodiments the clearance between the outer surface 242 of the movable element 240 and the bore 222 is about 0.005 mm per side, about 0.010 mm per side, about 0.015 mm per side, about 0.020 mm per side, about 0.025 mm per side, about 0.030 mm per side, about 0.035 mm per side, about 0.040 mm per side, about 0.045 mm per side, about 0.050 mm per side, or more than 0.050 mm per side. It should be understood that the seal between the outer surface 242 of the movable element 240 and the bore 222 is substantially airtight in some embodiments, but an airtight seal is not required in all valve embodiments.

In this embodiment, the movable element 240 becomes disposed within the bore 222 by pressing the movable element 240 past the first lip 223 and into the bore 222. Thereafter, the first lip 223 serves to restrict the movable element 240 from exiting the bore 222 during normal use because the inner diameter of the first lip 223 is smaller than the outer diameter of the movable element 240. The first lip 223 can be beveled to facilitate the insertion of the movable element 240 into the bore 222. In some embodiments, other configurations can be used to restrict the movable element 240 from exiting the bore 222. For example, without limitation, an internal snap ring can be used instead of the first lip 223. The internal snap ring can be install in the bore 222 at the first end portion 212 after the movable element 240 has been placed within the bore 222.

Referring to FIG. 5 in particular, the pressure differential relief valve 200 is shown with the movable element 240 in an intermediate position. That is, the movable element 240 is positioned longitudinally near the middle of the valve body 210, in an intermediate position. In this configuration, the movable element 240 substantially prevents gas flow through the valve 200 between the first end portion 212 and the second end portion 216, because there is no open path by which gas may flow through the valve 200. Therefore, in this configuration essentially no air (or other gas) can flow through the valve 200 between a first external region that is near the first end portion 212 and a second external region that is near the second end portion 216.

This configuration of the valve 200, with the movable element 240 in the intermediate position, is the configuration for normal operations of the valve 200. That is, the valve 200 is in this general configuration when there are no "excessive" pressure differentials between the first external region that is near the first end portion 212 and the second external region that is near the second end portion 216 (e.g., $P_i$ and $P_e$ of FIGS. 1 and 3).

Still referring to FIG. 5, when $P_e$ is not equal to $P_i$ the air pressure on the movable element's first end surface 244 is not equal to the air pressure on the movable element's second end surface 246. Consequently, the movable element 240 may be urged to move longitudinally within the bore 222 of the valve body 210, either towards the first end portion 212 or towards the second end portion 216.

For example, when $P_e$ is greater than $P_i$, the movable element 240 is urged to move towards the second end portion 216. The resilient member 230 resists such movement of the movable element 240 towards the second end portion 216. In result, the resilient member 230 will be deflected (e.g., compressed) a certain distance by the movable element 240. The distance that the resilient member 230 will be deflected will be the distance that results in a counter force from the resilient member 230 that essentially equals the differential in force that is applied onto the movable element 240 as a result of $P_e$ being greater than $P_1$. In other words, the force differential from $P_e$ being greater than $P_i$ will cause the movable element 240 to keeping moving towards the second end portion 216 until the resistance from the deflection of the resilient member 230 balances the force differential from $P_e$ being greater than $P_1$.

In the opposite scenario, $P_e$ is less than $P_1$. In that case, the force exerted by $P_i$ on the second end surface 246 is greater than the force exerted by $P_e$ on the first end surface 244. Therefore, the movable element 240 may be urged by the force differential to move towards the first end portion 212. However, the weight of the movable element 240 will resist the urging of the force differential. When the force differential is less than the weight of the movable element 240, the movable element will not move and will remain in the intermediate position where no airflow path through the valve 200 exists. However, when the force differential becomes greater than the weight of the movable element 240, the movable element 240 will tend to move within the bore 222 of the valve body 210 towards the first end portion 212 until the movable element's first end surface 244 comes into contact with the first lip 223. As the movable element 240 moves in that manner, the movable element 240 may become separated from the resilient element 230 in some embodiments.

Referring now to FIG. 8, the pressure differential relief valve 200 is shown in a first configuration in which the valve 200 relieves an excess differential pressure between $P_i$ and $P_e$. In this example configuration, the force exerted by $P_i$ on the movable element's second end surface 246 is greater than the force exerted by $P_e$ on the movable element's first end surface 244. Such would be the case, for example (referring to FIG. 1), when the pressure within the airspace 122 of the reservoir 120 is greater than the ambient pressure external to the reservoir 120.

In this example configuration, the force related to $P_i$ is greater than the force related to $P_e$, by more than the weight of the movable element 240. Hence, the force differential is enough to overcome the weight of the movable element 240, and the movable element 240 is caused to move within the bore 222 of the valve body 210 towards the first end portion 212, until the movable element's first end surface 244 comes close to or into contact with the first lip 223.

In this configuration, the movable element 240 has moved into a position such that an air pathway 250 exists through the valve 200. This configuration is also referred to herein as an active configuration because air is allowed to actively flow through the valve 200 along pathway 250 in this configuration. The pathway 250 allows air to flow from the second end portion 216 towards the first end portion 212, to thereby relieve an excess pressure differential between the second end opening 217 (which is also confluent with the region exterior to the valve 200 that has the pressure P) and the first end opening 213 (which is also confluent with the region exterior to the valve 200 that has the pressure $P_e$).

The pathway 250 begins at or near the second end portion 216 of the valve body 210. Air (or another fluid) from the region exterior to the second end portion 216 (which may be an internal airspace of a reservoir in some implementations) can flow into the valve 200 by entering through the second end opening 217, or through the second gas passageway external port 218, or both. From those entrances, the air can then flow into the open internal bore space 222 of the valve body 210. From the bore 222, the air can flow into the first gas passageway 224 via a first gas passageway internal port 227. The air can exit the valve 200 through the first gas passageway external port 214 at the first end portion 212. As described above, alternative valve embodiments may be configured with two or more such gas passageways so as to provide passageway redundancy or a larger flow passageway space.

The pathway 250 will continue to remain open as long as the differential force (the force exerted by $P_i$ on the movable element's second end surface 246 minus the force exerted by $P_e$ on the movable element's first end surface 244) is at least slightly more than the weight of the movable element 240. After the pressure differential has been sufficiently reduced by air flowing along the pathway 250, the weight of the movable element 240 will overcome the reduced force differential on the movable element 240, such that the movable element 240 will move towards the intermediate position (e.g., refer to FIG. 5). The first gas passageway internal port 227 will then be blocked by the movable element 240. In this manner, the valve 200 can reset itself after relieving an excess differential pressure. The valve 200 is then operable to relieve another instance of excess differential pressure if needed.

Referring now to FIG. 9, the pressure differential relief valve 200 is shown in a second configuration in which an excess differential pressure between $P_i$ and $P_e$ can be relieved. In this example configuration, the force exerted by $P_e$ on the movable element's first end surface 244 is greater than the force exerted by $P_i$ on the movable element's second end surface 246. Such would be the case, for example (referring to FIG. 1), when the ambient pressure external to the reservoir 120 is greater than the pressure within the airspace 122 of the reservoir 120.

In this example configuration, the force related to $P_e$ is greater than the force related to $P_i$, thereby urging the movable element 240 to move within the bore 222 of the valve body 210 towards the second end portion 216. In doing so, the movable element 240 deflects (e.g., compresses) the resilient member 230. As the resilient member 230 deflects, the resilient member 230 exerts a counterforce on the movable element 240 that is essentially equal to the linear distance of the deflection multiplied by the spring rate of the resilient member 230. Therefore, the movable element 240 will compress the resilient member 230 to an extent to where the counterforce from the resilient member 230 essentially balances the force differential exerted on the movable element 240 from the pressure differential between $P_e$ and $P_i$.

In this configuration, the movable element 240 has moved into a position such that an air pathway 260 exists through the valve 200. This configuration is an active configuration because air is allowed to actively flow through the valve 200 along pathway 260 in this configuration. The pathway 260 allows air to flow from the first end portion 212 towards the second end portion 216, to thereby relieve an excess pressure differential between the first end opening 213 (which is also confluent with the region exterior to the valve 200 that has the pressure $P_e$) and the second end opening 217 (which is also confluent with the region exterior to the valve 200 that has the pressure $P_i$).

The pathway 260 begins at the first end portion 212 of the valve body 210. The air from the region exterior to the first end portion 212 can flow into the valve 200 by entering through the first end opening 213, or through the first gas passageway external port 214, or both. From those entrances, the air can then flow into the open internal bore space 222 of the valve body 210. From the bore 222, the air can flow into the second gas passageway 226 though a second gas passageway internal port 228. The air can exit the valve 200 through the second gas passageway external port 218 at the second end portion 216. As described above, alternative valve embodiments may be configured with two or more such gas passageways so as to provide passageway redundancy or a larger flow passageway space.

The pathway 260 will continue to remain open as long as the differential force exerted by $P_e$ on the movable element's first end surface 244 minus the force exerted by $P_i$ on the movable element's second end surface 246 is sufficient to activate the valve 200. The amount of differential force needed to activate the valve 200 in this configuration is the amount needed to open the second gas passageway internal port 228 to the bore 222. The second gas passageway internal port 228 will be open to the bore 222 as long as the movable element 240 is positioned sufficiently towards the second end portion 216. That is, when movable element's first end surface 244 is located sufficiently towards the second end portion 216, the second gas passageway internal port 228 will be open to the bore 222, and the pathway 260 will exist.

When the differential force exerted by $P_e$ on the movable element's first end surface 244 in comparison to the force exerted by $P_i$ on the movable element's second end surface 246 is sufficiently reduced (such as by air flowing along the pathway 260 to at least partially alleviate the pressure differential), the valve 200 will tend to deactivate. In this context, deactivation means the closure (blockage) of the second gas passageway internal port 228 by the movable element 240. The valve 200 will tend to deactivate when the pressure differential between $P_e$ and $P_i$ has been reduced such that the deflection of the resilient member 230 is no longer great enough to open the second gas passageway internal port 228 by allowing the movable element 240 to be positioned sufficiently towards the second end portion 216. In that case, the movable element 240 will move towards the intermediate position where the movable element 240 blocks both of the first gas passageway internal port 227 and the second gas passageway internal port 228 (e.g., refer to FIG. 5). In this manner, the valve 200 resets itself after relieving an excess differential pressure. The valve 200 is then operable to relieve another instance of excess differential pressure if needed.

Referring now to FIG. 10, a first example graph 300 can be used to further describe the operations of the pressure differential relief valves provided herein. The graph 300 is a graph of differential pressures between an interior space of a reservoir and an ambient space that is external to the reservoir. However, it should be understood that the graph 300 also pertains generally to, for example, (i) a first region that is exterior to the valve and proximate to a first end portion of the valve, in comparison to (ii) a second region that is exterior to the valve body and proximate to a second end portion of the valve.

The midpoint 310 of the graph 300 represents a zero differential between the pressures of the reservoir interior and the ambient space. The portion of the graph 300 to the left of the midpoint 310 represents a negative pressure differential between the pressures of the reservoir interior and the ambient space. In other words, a vacuum exists in the reservoir interior. The portion of the graph 300 to the right of the midpoint 310 represents a positive pressure differential between the pressures of the reservoir interior and the ambient space.

When a positive pressure differential exists between the pressures of the reservoir interior and the ambient space (as represented on the right portion of the graph 300), at some level of pressure differential the weight of the valve's movable element will be overcome (e.g., as described above in reference to FIG. 8). That level of pressure differential is represented in graph 300 at a first activation differential pressure 320. At that level of positive differential pressure, and for levels that are greater (represented by a line 324), the movable element will become positioned so as to allow airflow through the valve to relieve the excess positive pressure within the reservoir interior. When the positive pressure differential drops down to below the first activation differential pressure 320, the valve will then deactivate (close). In the context of the medical fluid system 100 of FIG. 1, for example, the first activation differential pressure 320 may be at a level within a range of about 0 mmHg to about 4 mmHg, but other levels are also envisioned for medical fluid reservoirs, and for implementations in other types of fluid systems.

When a negative pressure differential (vacuum) exists between the pressures of the reservoir interior and the ambient space (as represented on the left portion of the graph 300), at some level of pressure differential the resilient member within the valve will be deflected to the extent that air can flow through the valve (e.g., as described above in reference to FIG. 9). That level of negative pressure differential is represented in graph 300 at a second activation differential pressure 330. At that level of negative differential pressure and for levels that are more negative (represented by a line 334), the movable element will become positioned so as to allow an airflow through the valve to relieve the excess negative pressure within the reservoir interior. When the negative pressure differential drops down to below the second activation differential pressure 330, the valve will then deactivate (close).

At differential pressures between the first activation differential pressure 320 and the second activation differential pressure 330 the valve is deactivated (closed). This range of differential pressures is represented by an operative differential pressure range 340. The operative differential pressure range 340 may also be considered the designed operating range for the fluid system in which the pressure differential relief valves provided herein are installed.

The first activation differential pressure 320 and the second activation differential pressure 330 may be selected according to the design parameters of the fluid system in which the pressure differential relief valves provided herein reside. To adjust the first activation differential pressure 320, the weight of the movable element of the valve may be selected. A heavier movable element will have a higher first activation differential pressure 320 than a lighter movable element. To adjust the second activation differential pressure 330, in some valve embodiments the spring constant of the resilient element of the valve may be selected. For example, a resilient element with a higher spring constant will have a more negative second activation differential pressure 330 than a resilient element with a lower spring constant. In some embodiments, the second activation differential pressure 330 can also be selected based on adjusting the length of the second gas passageway. In some embodiments, the length of the movable element (or a portion thereof) may also be used to select a desirable second activation pressure 330. In some embodiments, a suitable combination of such design factors can be strategically selected to configure a differential pressure relief valve with the operational characteristics that are desired for a particular fluid system. It should be understood from the description herein that the differential pressure relief valves provided herein are configurable in a wide variety of designs so as to be well suited for implementation in a wide variety of fluid systems.

Referring now to FIG. 11, a second example graph 400 can be used to further describe the operations of the pressure differential relief valves provided herein. The second example graph 400 relates to a different differential pressure relief valve than the valve that the first example graph 300 relates to. However, the scale of the second example graph 400 is essentially the same as the scale of the first example graph 300. Again, the midpoint 410 of the graph 400 represents a zero differential between the pressures of the reservoir interior and the ambient space.

As with the first example graph 300, the second example graph 400 includes a first activation differential pressure 420. At that level of positive differential pressure, and for levels that are greater (represented by a line 424), the movable element will tend to become positioned so as to allow an airflow through the valve to relieve the excess positive pressure within the reservoir interior. When the positive pressure differential drops down to below the first activation differential pressure 420, the valve will then tend to deactivate (close).

It can be seen by comparing the first example graph 300 and the second example graph 400 that the first activation differential pressure 420 is higher than the first activation differential pressure 320. Therefore, it can be determined that, in some embodiments the weight of the movable element of the valve represented by the second example graph 400 is heavier than the movable element of the valve represented by the first example graph 300. However, it should be understood that the respective surface areas of the ends of the movable element (which, in some embodiments, may be dissimilar) can also affect the respective activation pressure levels.

The second example graph 400 includes a second deactivation differential pressure 430 that is analogous to the second deactivation differential pressure 330 of graph 300. It can be seen by comparing the first example graph 300 and the second example graph 400 that the second activation differential pressure 430 is less negative than the second activation differential pressure 330. Therefore, it can be determined that, in some embodiments, the spring constant of the valve represented by graph 400 is less than the spring constant of the valve represented by graph 300. However, it should be understood that the respective surface areas of the ends of the movable element (which, in some embodiments, may be dissimilar) can also affect the respective activation pressure levels. The second activation pressure 430 can also be selected based on adjusting the length of the second gas passageway (e.g., second gas passageway 226 of FIG. 9). It can be understood that making the second gas passageway longer will move the second activation pressure 430 to a less negative amount. Conversely, making the second gas passageway shorter will move the second activation pressure 430 to a more negative amount. In some embodiments, the length of the movable element (or a portion thereof) may also be used to select a desirable second activation pressure 430.

The pressure differential valves provided herein perform both positive and negative pressure relief in single valve construct consisting of only three parts. The activation levels of positive and negative pressure relief can be selected readily and independently of each other. In other words, the valve's performance can be conveniently tuned to provide desired levels of positive and negative differential pressure relief.

Figure 12B:
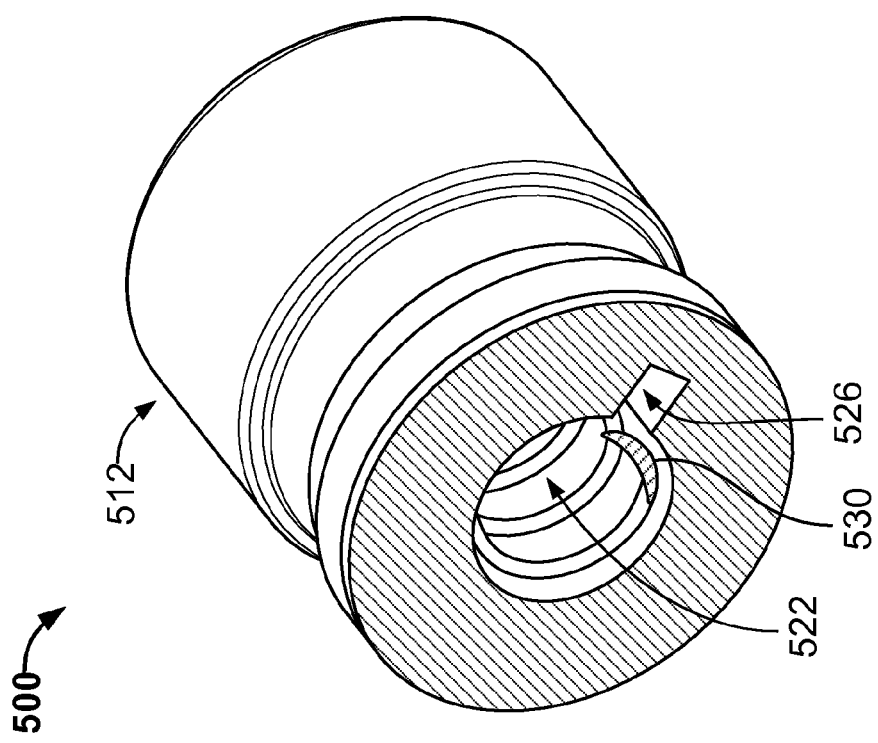
FIGS. 12B-12F are a series of transverse cross-sectional views taken at different locations of the pressure differential relief valve of FIG. 12A.
Figure 12A:
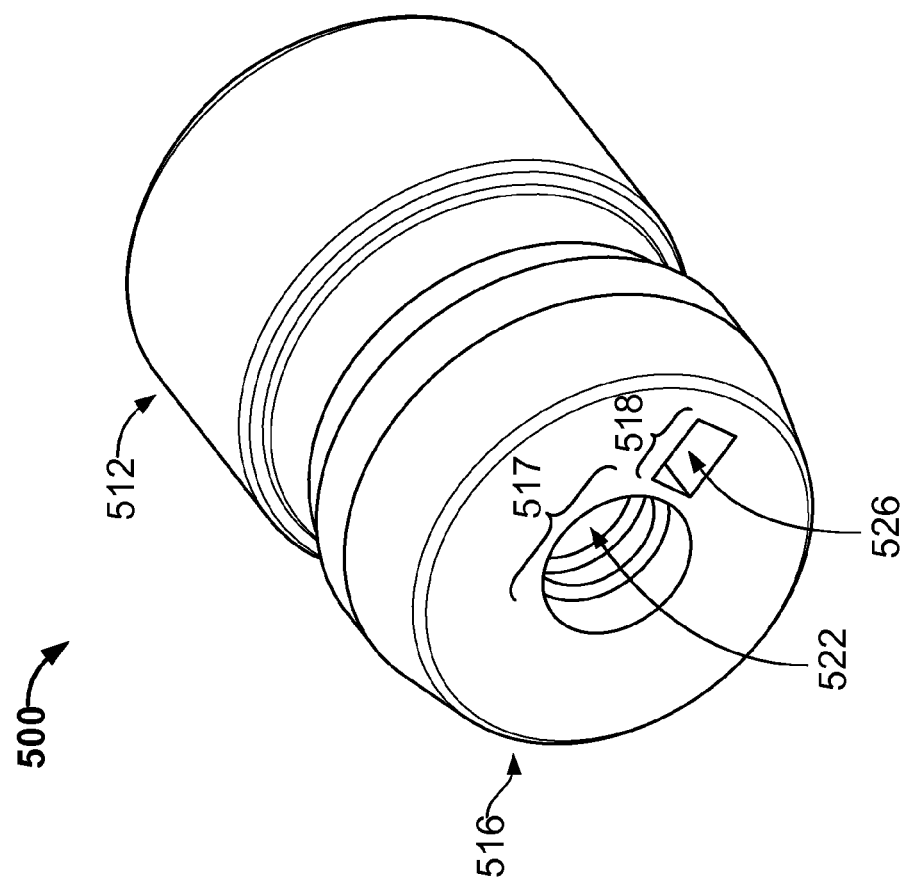
FIG. 12A is a perspective view of an example pressure differential relief valve in accordance with some embodiments provided herein.

FIG. 12A is a perspective view of an example pressure differential relief valve 500 having a first end portion 512 and a second end portion 516. FIGS. 12B-12F are a series of transverse cross-sectional views taken at different locations of the pressure differential relief valve 500 that are progressive farther from the second end portion 516 and closer to the first end portion 512.

As shown in FIG. 12A, the second end portion 516 includes a second end opening 517 and a second gas passageway external port 518. The second end opening 517 is confluent with a region that is external to the valve 500 and adjacent to the second end portion 516. The second end opening 517 is also confluent with an open interior bore space 522. Similarly, the second gas passageway external port 518 is confluent with the region that is external to the valve 500 and adjacent to the second end portion 516. The second gas passageway external port 518 is also confluent with a second gas passageway 526.

Figure 12D:
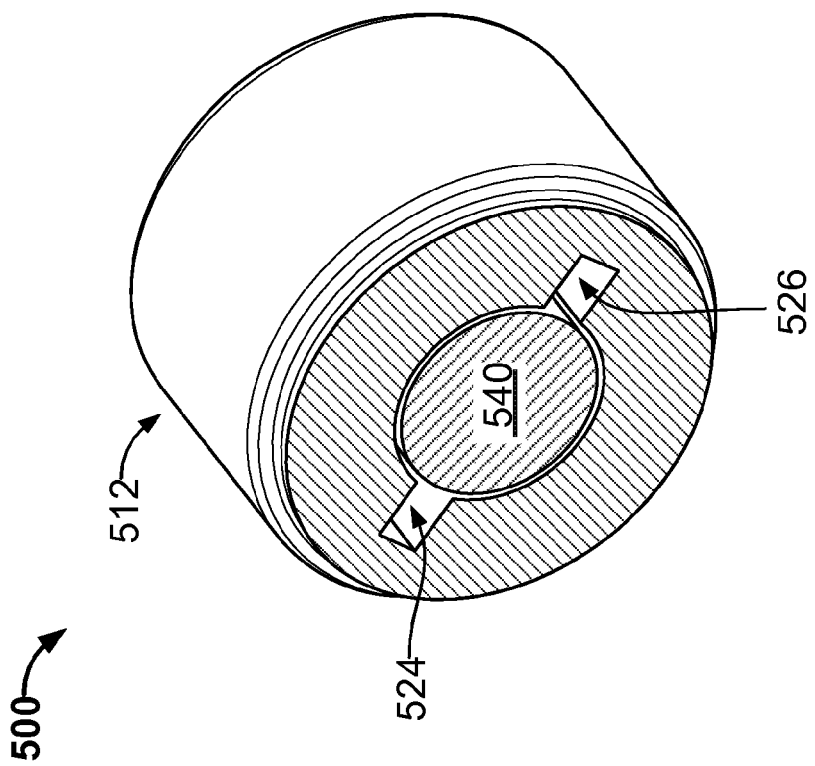
Figure 12C:
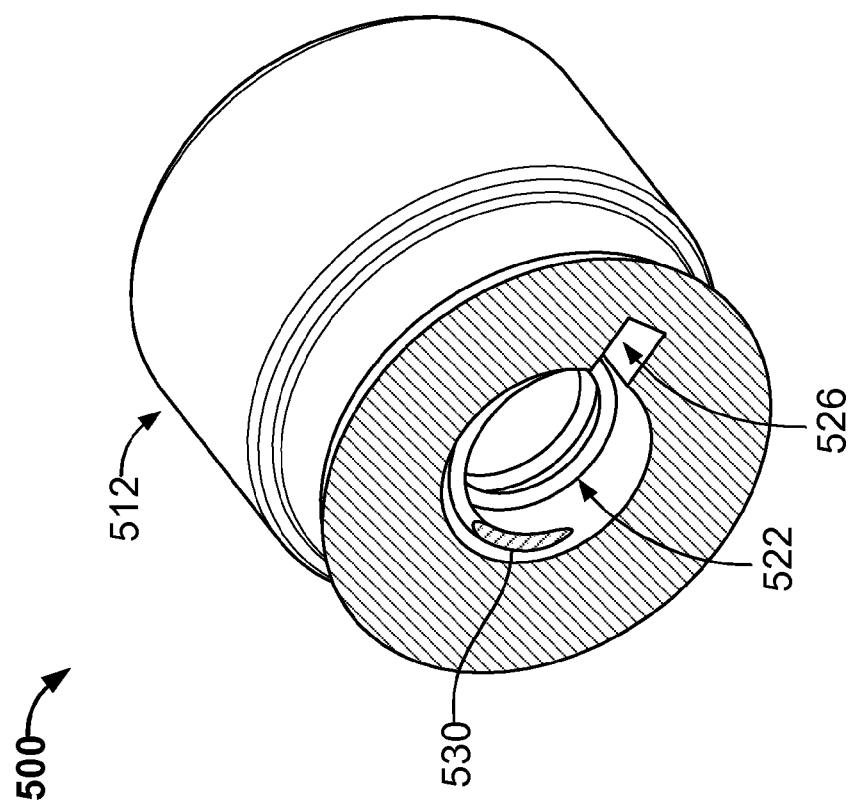
Figure 12F:
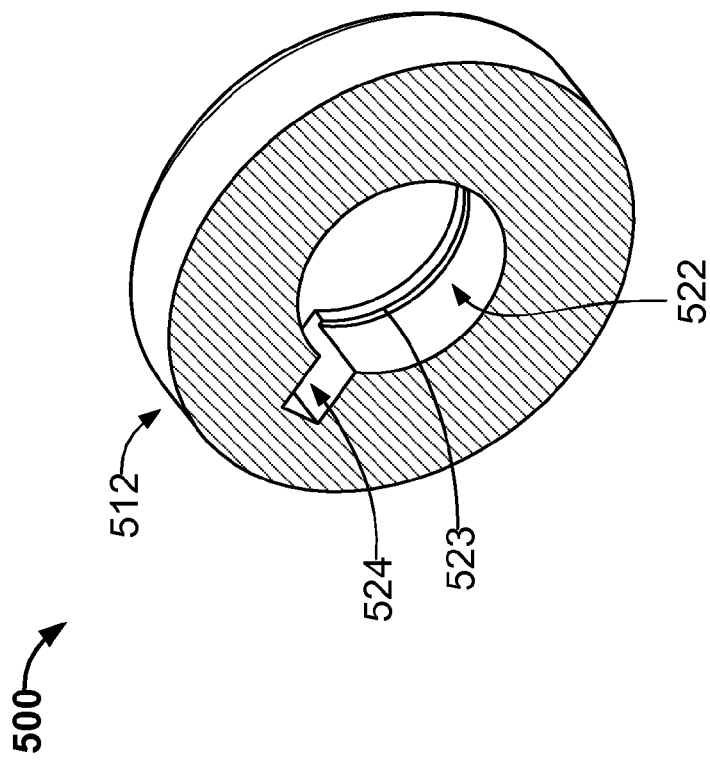

The transverse cross-sectional views of FIGS. 12B and 12C show the valve 500 with the end portion 516 removed. The bore 522 and the second gas passageway 526 are still visible. A resilient member 530 within the bore 522 is also visible.

The transverse cross-sectional view of FIG. 12D also still shows the second gas passageway 526. In addition, a movable element 540 and a first gas passageway 524 are now visible.

Figure 12E:
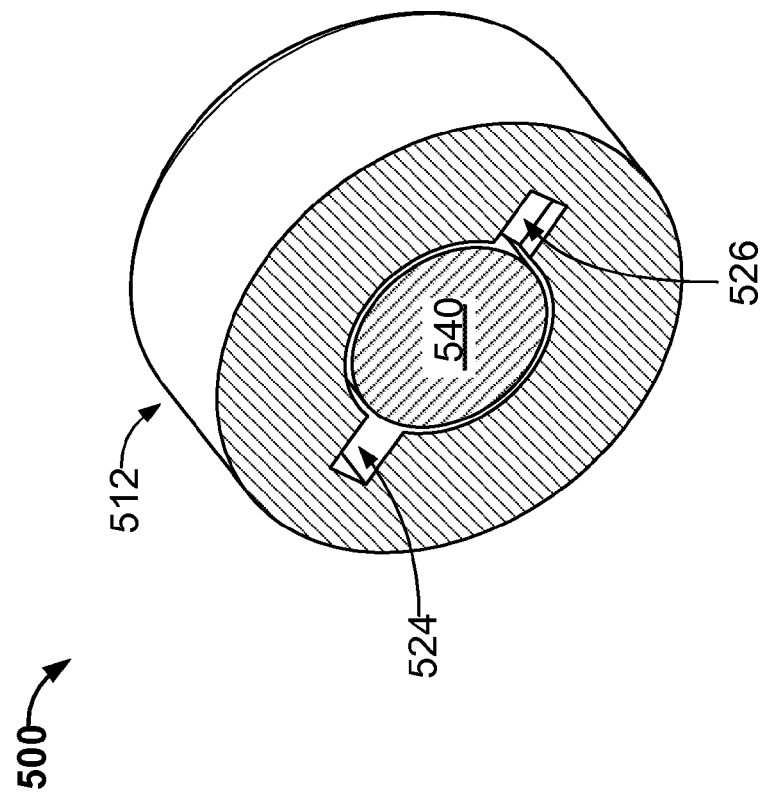

The transverse cross-sectional view of FIG. 12E shows termination of the second gas passageway 526. The movable element 540 and the first gas passageway 524 are still visible.

The transverse cross-sectional view of FIG. 12E shows the first gas passageway 524, the bore 522, and a first lip 523 that serves to restrain the movable element 540 within the bore 522, but the movable element 540 and the first gas passageway 524 are no longer visible.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A pressure differential relief valve for a medical fluid reservoir, the valve comprising:
  a valve body having a structure configured to mate with the medical fluid reservoir, the valve body including a first end portion and a second end portion, the valve body defining an open interior bore space within the valve body, the valve body defining first and second gas passageways that are configured to allow a first exterior region that is outside of the valve body and proximate to the first end portion to be in fluid communication through the valve body with a second exterior region that is outside of the valve body and proximate to the second end portion;
  a resilient member that is at least partially disposed within the open interior bore space; and
  a movable element that is at least partially disposed within the open interior bore space, the movable element being movable within the open interior bore space at least between (i) a first end position that is closer to the first end portion than to the second end portion, (ii) a second end position that is closer to the second end portion than to the first end portion, and (iii) an intermediate position that is between the first and second end positions,
  wherein, when the movable element is in the intermediate position, the movable element substantially prevents fluid communication through the valve body between the first exterior region and the second exterior region,
  wherein when the movable element is in the first end position the first exterior region and the second exterior region are in fluid flow communication through at least the first gas passageway,
  wherein when the movable element is in the second end position the first exterior region and the second exterior region are in fluid flow communication through at least the second gas passageway, and wherein when the movable element is in the second end position the movable element has deflected the resilient member,
  the valve body having an overall longitudinal length that extends directionally between the first and second end portions, the first gas passageway having a first longitudinal length that extends directionally between the first and second end portions, the second gas passageway having a second longitudinal length that extends directionally between the first and second end portions, wherein the first longitudinal length is less than the overall longitudinal length, wherein the second longitudinal length is less than the overall longitudinal length, and wherein a sum of the first longitudinal length and the second longitudinal length is greater than the overall longitudinal length.

2. The valve of claim 1, wherein when the atmospheric pressures at the first and second exterior regions are equal the movable element is biased to be in contact with the resilient member.

3. The valve of claim 1, wherein the movable element is spaced apart from the resilient member when the movable element is in the first end position.

4. The valve of claim 1, wherein the first end portion defines a first end opening and the second end portion defines a second end opening, wherein an atmospheric pressure at the first exterior region can be exerted on a first surface of the movable element at least through the first end opening to thereby urge the movable element to move towards the second end position, and wherein an atmospheric pressure at the second exterior region can be exerted on a second surface of the movable element at least through the second end opening to thereby urge the movable element to move towards the first end position.

5. The valve of claim 4, wherein the valve is configured such that differences between the atmospheric pressure at the first exterior region and the atmospheric pressure at the second exterior region can cause the movable element to move from the intermediate position to the first or second end position to thereby reduce the differences between the atmospheric pressure at the first exterior region and the atmospheric pressure at the second exterior region.

6. The valve of claim 1, the movable element having a length extending directionally between the first and second end portions, wherein the sum of the first longitudinal length added to the second longitudinal length minus the overall length of the valve body is less than the length of the movable element.

7. The valve of claim 1, wherein the resilient member is a spring.

8. The valve of claim 7, wherein the resilient member is a coil spring.

9. A medical fluid reservoir system comprising:
  a reservoir shell, the reservoir shell defining an interior space inside of the reservoir shell that is configured to contain a medical fluid and an exterior space that is outside of the reservoir shell; and
  a differential pressure relief valve that is coupled to the reservoir shell, the differential pressure relief valve comprising:
    a valve body including a first end portion at least partially exposed to the exterior space and a second end portion at least partially exposed to the interior space, the valve body defining an open interior bore space within the valve body,
    a resilient member that is at least partially disposed within the open interior bore space; and
    a movable element that is at least partially disposed within the open interior bore space, the movable element being movable within the open interior bore space at least between (i) a first end position that is closer to the first end portion than to the second end portion, (ii) a second end position that is closer to the second end portion than to the first end portion, and (iii) an intermediate position that is between the first and second end positions, wherein when the movable element is in the intermediate position the movable element prevents fluid communication through the valve body between the interior and exterior spaces, wherein when the movable element is in the first end position the interior and exterior spaces are in fluid flow communication through at least a first gas passageway, wherein when the movable element is in the second end position the interior and exterior spaces are in fluid flow communication through at least a second gas passageway, and wherein when the movable element is in the second end position the movable element has deflected the resilient member, the valve body having an overall longitudinal length extending directionally between the first and second end portions, the first and second gas passageways having longitudinal lengths extending directionally between the first and second end portions, wherein the lengths of each of the first and second gas passageways are less than the overall longitudinal length of the valve body, and wherein the combined lengths of the first and second gas passageways are greater than the overall longitudinal length of the valve body.

10. The medical fluid reservoir of claim 9, wherein the valve body defines the first and second gas passageways that are each configured to allow the exterior space to be in fluid communication through the valve body with the interior space.

11. The medical fluid reservoir of claim 10, wherein when the movable element is in the first end position the interior and exterior spaces are in fluid flow communication through at least the first gas passageway, and wherein when the movable element is in the second end position the interior and exterior spaces are in fluid flow communication through at least the second gas passageway.

12. The valve of claim 9, the movable element having a length extending directionally between the first and second end portions, wherein the combined lengths of the first and second gas passageways minus the overall length of the valve body is less than the length of the movable element.

13. The medical fluid reservoir of claim 9, wherein the medical fluid comprises blood.

14. The medical fluid reservoir of claim 13, wherein the medical fluid reservoir is configured to have an air space disposed within the interior space in addition to having the blood within the interior space.

15. The medical fluid reservoir of claim 9, wherein the differential pressure relief valve is configured such that differences between the atmospheric pressure of the exterior space and the atmospheric pressure of the interior space can cause the movable element to move from the intermediate position to the first or second end position to thereby reduce the differences between the atmospheric pressure at the exterior space and the atmospheric pressure at the interior space.

* * * * *

UNITED STATES PATENT AND TRADEMARK OFFICE
CERTIFICATE OF CORRECTION

PATENT NO. : 9,435,450 B2  
APPLICATION NO. : 14/171925  
DATED : September 6, 2016  
INVENTOR(S) : Gregory Peter Muennich It is certified that error appears in the above-identified patent and that said Letters Patent is hereby corrected as shown below:

On the Title Page

Item (71) Column 1 Line 2 delete "Terumo Cardiovascular Systems, Inc." and insert --Terumo Cardiovascular Systems Corporation--;

Item (73) Column 1 Line 3 delete "Terumo Cardiovascular Systems, Inc." and insert --Terumo Cardiovascular Systems Corporation--.

Signed and Sealed this  
Twenty-ninth Day of May, 2018

Andrei Iancu  
*Director of the United States Patent and Trademark Office*